(12) United States Patent
McCoy

(10) Patent No.: US 7,901,932 B2
(45) Date of Patent: Mar. 8, 2011

(54) **METHODS AND COMPOSITIONS FOR RAPIDLY DETECTING AND QUANTIFYING VIABLE *LEGIONELLA***

(75) Inventor: William F. McCoy, Naperville, IL (US)

(73) Assignee: Phigenics, LLC, Naperville, IL (US)

( * ) Notice: Subject to any disclaimer, the term of this patent is extended or adjusted under 35 U.S.C. 154(b) by 706 days.

(21) Appl. No.: 11/686,732

(22) Filed: Mar. 15, 2007

(65) Prior Publication Data

US 2007/0218522 A1 Sep. 20, 2007

Related U.S. Application Data

(63) Continuation-in-part of application No. 11/376,516, filed on Mar. 15, 2006.

(60) Provisional application No. 60/033,071, filed on Mar. 17, 2005.

(51) Int. Cl.
*C12M 1/34* (2006.01)
*C12Q 1/04* (2006.01)
*C12Q 1/18* (2006.01)

(52) U.S. Cl. ........ 435/287.7; 435/32; 435/34; 435/287.1

(58) Field of Classification Search ........................ None
See application file for complete search history.

(56) References Cited

U.S. PATENT DOCUMENTS

| | | | |
|---|---|---|---|
| 3,787,290 A * | 1/1974 | Kaye | 435/40 |
| 3,890,202 A * | 6/1975 | Bergeron | 435/304.1 |
| 4,468,332 A | 8/1984 | Peacock et al. | |
| 4,514,509 A | 4/1985 | Kohler et al. | |
| 4,587,213 A * | 5/1986 | Malecki | 435/39 |
| 4,659,484 A | 4/1987 | Worley et al. | |
| 4,692,407 A * | 9/1987 | Jordan et al. | 435/36 |
| 4,722,891 A | 2/1988 | Drutz et al. | |
| 4,778,758 A * | 10/1988 | Ericsson et al. | 435/32 |
| 4,780,407 A | 10/1988 | Strosberg et al. | |
| 4,810,644 A | 3/1989 | Tchen et al. | |
| 4,851,333 A | 7/1989 | Goldstein et al. | |
| 4,861,489 A | 8/1989 | Swift et al. | |
| 4,868,110 A * | 9/1989 | DesRosier et al. | 435/34 |
| 4,931,547 A | 6/1990 | Hoffman et al. | |
| 4,940,024 A | 7/1990 | Grabietz | |
| 5,004,682 A | 4/1991 | Roberts et al. | |
| 5,108,745 A | 4/1992 | Horwitz | |
| 5,168,546 A | 12/1992 | Laperriere et al. | |
| 5,236,600 A | 8/1993 | Hutchins | |
| 5,248,594 A | 9/1993 | Aloisio et al. | |
| 5,298,392 A * | 3/1994 | Atlas et al. | 435/6 |
| 5,339,889 A | 8/1994 | Bigham | |
| 5,349,874 A | 9/1994 | Schapira et al. | |
| 5,486,630 A | 1/1996 | Lee et al. | |
| 5,491,225 A | 2/1996 | Picone et al. | |
| 5,503,997 A | 4/1996 | Lee et al. | |
| 5,529,924 A | 6/1996 | Lee et al. | |
| 5,541,308 A | 7/1996 | Hogan et al. | |
| 5,547,842 A | 8/1996 | Hogan et al. | |
| 5,569,586 A | 10/1996 | Pelletier et al. | |
| 5,593,841 A | 1/1997 | Hogan et al. | |
| 5,595,874 A | 1/1997 | Hogan et al. | |
| 5,614,388 A | 3/1997 | Picone et al. | |
| 5,660,998 A | 8/1997 | Naumann et al. | |
| 5,674,684 A | 10/1997 | Hogan et al. | |
| 5,677,127 A | 10/1997 | Hogan et al. | |
| 5,677,128 A | 10/1997 | Hogan et al. | |
| 5,677,129 A | 10/1997 | Hogan et al. | |
| 5,679,520 A | 10/1997 | Hogan et al. | |
| 5,683,876 A | 11/1997 | Hogan | |
| 5,691,149 A | 11/1997 | Hogan et al. | |
| 5,693,468 A | 12/1997 | Hogan et al. | |
| 5,693,469 A | 12/1997 | Hogan | |
| 5,714,321 A | 2/1998 | Hogan | |
| 5,808,277 A | 9/1998 | Dosani et al. | |
| 5,827,651 A | 10/1998 | Hogan et al. | |
| 5,834,197 A | 11/1998 | Parton | |
| 5,840,488 A | 11/1998 | Hogan | |
| 5,882,588 A | 3/1999 | Laberge | |
| 5,958,679 A | 9/1999 | Hogan et al. | |
| 5,968,739 A | 10/1999 | Macioszek et al. | |
| 5,985,935 A | 11/1999 | Kharazmi et al. | |
| 5,994,059 A | 11/1999 | Hogan et al. | |
| 6,021,803 A | 2/2000 | Nutsos | |
| 6,150,517 A | 11/2000 | Hogan et al. | |
| 6,172,029 B1 | 1/2001 | Mitzutani et al. | |
| 6,194,145 B1 | 2/2001 | Heidrich et al. | |
| 6,203,822 B1 | 3/2001 | Schlesinger et al. | |

(Continued)

FOREIGN PATENT DOCUMENTS

DE 29 36 294 6/1980

(Continued)

OTHER PUBLICATIONS

Bauer, et al., "Detection of *Legionella* Species in a Water Supply System Using Gene Probe Technique and Culture Method," *Zbl. Hyg.* 190: 78-83 (1990).

Bartie, et al. "Identification Methods for *Legionella* from Environmental Samples," Water Research, Elsevier, Amsterdam, NL, 37: 6 (Mar. 2003).

Chang, et al., "Comparison of Multiplex PCR and Culture for Detection of *Legionella* in Cooling Tower Water Samples," *Southeast Asian J. Trop Med Public Health*, 26(2): 258-262, (1995).

Cloud, et al., "Detection of *Legionella* Species in Respiratory Specimens using PCR with Sequencing Confirmation," *J. Clin. Microbiol.*, 1709-1712 (2000).

Feeley, et al., "Primary Isolation Media for Legionnaire's Disease Bacterium," *J. Clin. Microbiol.*, 8: 320-325, (1978).

Fields, et al. "*Legionella* and Legionnaires' Disease : 25 Years of Investigation," *Clin. Microbiol. Rev.*, 15(3): 506-526 (2002).

(Continued)

*Primary Examiner* — Lisa J Hobbs

(74) *Attorney, Agent, or Firm* — Barnes & Thornburg LLP; Alice O. Martin

(57) ABSTRACT

Methods and compositions detect and quantify viable *Legionella* and other heterotrophic aerobic bacteria. Dipslides that include an absorbent medium, growth promoting, and growth selective substances are useful in rapid detection and quantification of microcolonies of *Legionella*. Most probable number method of detection and quantification of *Legionella* are disclosed.

4 Claims, 3 Drawing Sheets

U.S. PATENT DOCUMENTS

Figure 1:
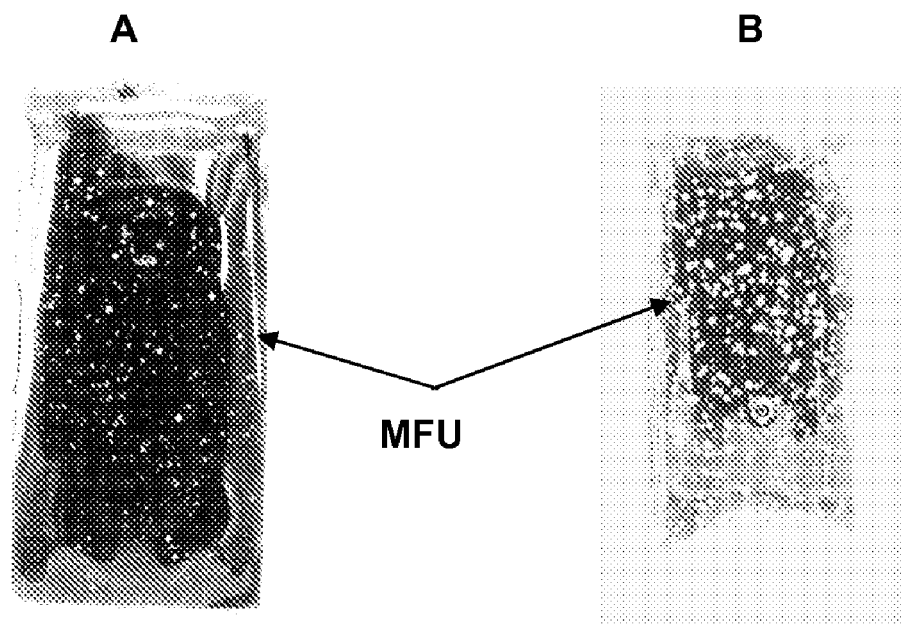

| | | | |
|---|---|---|---|
| 6,251,609 B1 | 6/2001 | Brink et al. | |
| 6,268,326 B1 | 7/2001 | Mitzutani et al. | |
| 6,399,056 B1 | 6/2002 | Ono et al. | |
| 6,512,105 B1 | 1/2003 | Hogan et al. | |
| 6,579,859 B1 | 6/2003 | Whitekettle et al. | |
| 6,660,494 B2 | 12/2003 | Schabert et al. | |
| 6,669,901 B2 | 12/2003 | Eynard et al. | |
| 6,673,248 B2 | 1/2004 | Chowdhury | |
| 6,770,192 B2 | 8/2004 | Peterson | |
| 2005/0061197 A1* | 3/2005 | Nalepa | 106/15.05 |
| 2005/0064444 A1 | 3/2005 | Beimfohr et al. | |

FOREIGN PATENT DOCUMENTS

| | | |
|---|---|---|
| EP | 306206 A1 * | 3/1989 |
| FR | 2 801 677 | 6/2001 |
| GB | 2 141 136 | 12/1984 |
| WO | WO 94/17175 | 8/1994 |
| WO | WO 00/10584 | 3/2000 |
| WO | WO 02/102824 | 12/2002 |
| WO | WO 2005/021731 | 3/2005 |
| WO | WO 2005/085464 | 9/2005 |

OTHER PUBLICATIONS

Furuhata, et al., "Colony Hybridization Method for Rapid Detection of *Legionella* spp. biocontrol," *Science*, 4:89-92 (1999).

Grabow et al., "Most Probable Number Method for the Enumeration of *Legionella* Bacteria in Water," *Water Sci Technol; Water Science and Technology; Health-Related Water Microbiolgy*, 24:2, 143-147 (Apr. 1, 1990).

International Standard (ISO), "Water Quality—Detection and Enumeration of *Legionella*," First Edition, May 1, 1998, ISO 11731 (1998)(E).

McCoy. "Microbial Waterborne Pathogens." Chapter 5, *Legionella*, pp. 100-131 (ed. T.E. Cloete, et al.); *International Water Association*, IWA Publishing, London, UK. ISBN:1843390558 (2004).

McDade, et al., "Legionnaires' Disease: Isolation of a Bacterium and Demonstration of its Role in Other Respiratory Diseases," *N. Engl. J. Med.*, 287: 1197-1203 (1977). Abstract.

Satoh, et al. "Enumeration of *Legionella* CFU by Colony Hybridization Using Specific DNA Probes," *Appl Environ Microbiol.*, 68(12): 6466-70 (2002).

Vesey, "Detection of Viable *Legionella* in 5 Hours," *J. Appl. Bacteriol.*, 69(6): (1990). Abstract.

U.S. Department of Health and Human Services, "Procedures for the Recovery of *Legionella* from the Environment," Nov. 1994.

Alam et al., "Effect of Transport at Ambient Temperature on Detection and Isolation of *Vibrio cholerae* from Environmental Samples," *Applied and Environmental Microbiology*, 72 (3): 2185-2190 (2006).

Association of Water Technologies, "*Legionella* 2003: An update and statement by the Association of Water Technologies," McLean, VA, pp. 1-33, http://www.awt.org/Legionella03.pdf (2003).

Centers for Disease Control and Prevention, "Procedures for the Recovery of *Legionella* from the Environment," National Center for Infectious Diseases, Division of Bacterial and Mycotic Diseases, Respiratory Diseases Laboratory Section, Atlanta, GA, pp. 1-13, http://www.cdc.gov/legionella/files/LegionellaProcedures.pdf (2005).

Cooling Technology Institute, "Legionellosis Guideline: Best Practices for Control of *Legionella*," Houston, TX, pp. 1-12, http://www.cti.org/cgi-bin/download.pl (2008).

McCoy, Preventing Legionellosis, IWA Publishing, London, UK, pp. 1-152, ISBN: 1 843390 94 9 (2005).

McCoy et al., "A New Field Method for Enumerating Viable *Legionella* And Total Heterotrophic Aerobic Bacteria," Presentation at the 2007 Association of Water Technologies Convention and Exposition, Colorado Springs, CO, pp. 1-20, (2007).

McCoy et al., "A New Method to Measure Viable *Legionella* and Total Heterotrophic Aerobic Bacteria," Presented at the 2008 Cooling Technology Institute Annual Conference, Houston, TX, pp. 1-22 (2008).

McDaniels et al., "Holding Effects on Coliform Enumeration in Drinking Water Samples," *Applied and Environmental Microbiology*, 50 (4): 755-762 (1985).

Miller et al., "*Legionella* Prevalence in Cooling Towers: Association with Specific Biocide Treatments," *ASHRAE Transactions* CH 06-12-2, 112 (1): 1-11 (2006).

Pope et al., "Assessment of the Effects of Holding Time and Temperature on *Escherichia coli* Densities in Surface Water Samples," *Applied and Environmental Microbiology*, 69 (10): 6201-6207 (2003).

World Health Organization, "Heterotrophic Plate Counts and Drinking-Water Safety: The significance of HPCs for Water Quality and Human Health," IWA Publishing, London, UK, pp. 1-245, ISBN: 92 4 126226 9 (2003).

World Health Organization, "Guidelines for Drinking-water Quality—First Addendum to Third Edition, vol. 1—Recommendations," WHO Press, Geneva, Switzerland, pp. 1-515, ISBN: 92 4 154696 4 (2006).

World Health Organization, "*Legionella* and the Prevention of Legionellosis," WHO Press, Geneva, Switzerland, pp. 1-252, ISBN: 92 4 156297 8 (2007).

Vesey et al., "Rapid Enumeration of Viable *Legionella pneumophila* Serogroup 1," *Letters in Applied Microbiology*, 90 (10): 113-116 (1989).

International Search Report issued in PCT/US2006/009336 (2006).

* cited by examiner

METHODS AND COMPOSITIONS FOR RAPIDLY DETECTING AND QUANTIFYING VIABLE *LEGIONELLA*

This application is a continuation-in-part of U.S. Ser. No. 11/376,516 filed Mar. 15, 2006 which claims priority to U.S. Ser. No. 60/033,071 filed Mar. 17, 2005.

BACKGROUND

Legionnaires' disease is a common name for one of the several illnesses caused by *Legionella* or Legionnaires' disease bacteria (LDB). Legionellosis is the condition of being infected by *Legionella* bacteria which can cause serious pneumonia. By far, most legionellosis is the result of exposure to contaminated building water systems. Each year, hundreds of thousands of people suffer from these infections and many tens of thousands die from legionellosis or its complications.

About forty eight *Legionella* species with 70 serogroups have been classified. *L. pneumophila* is responsible for about 80%-85% of *Legionella* infections and serogroups 1 and 6 are responsible for two-thirds of *Legionella* infections. Other isolates and serogroups also contribute to *Legionella* infections. There are 15 serogroups of *L. pneumophila* and about 70 serogroups in total for *Legionella*. Some of the *Legionella* isolates and serogroups that cause infection include *L. longbeachae, L. bozemanii, L. micdadei, L. dumoffii, L. feeleii, L. wadsworthii*, and *L. anisa*. Two other genera have been proposed: *Fluoribacter* blue-white fluorescing species such as *L. bozemanii* and *Tatlockia* for the species *L. micdadei*.

*Legionella* is widely present at low levels in the environment: in lakes, streams, and ponds. Water heaters, potable water distribution systems, decorative fountains, spa baths, swimming pools, humidifiers, evaporative cooling water towers, and warm, stagnant water provide ideal conditions for the growth and transmission of the biological hazard. Warm, stagnant water provides ideal conditions for growth. At about 30° C.-50° C. (75°-122° F.) the microorganism can multiply significantly and rapidly within its protozoan host, mostly the aquatic protozoa including different genera of amoeba. Rust (iron), scale, and the presence of other microorganisms can also promote conditions that result in rapid growth of *Legionella*.

Preventive measures include regular maintaining and cleaning of building water systems such as cooling towers and evaporative condensers to prevent growth of *Legionella*, which should typically include for example, twice-yearly cleaning and periodic use of chlorine or other effective disinfectants; maintaining domestic water heaters at 60° C. (140° F.); and avoidance of conditions that allow water to stagnate, as, for example, large water-storage tanks exposed to heat from sunlight that produce warm conditions favorable to high levels of *Legionella* and its protozoan host.

Detection of *Legionella* by a "Standard Method", as mandated by many government-sponsored guidelines, codes of practice, standards, regulations or laws such as for example, the Occupational Safety and Health Administration (OSHA) guidelines, takes about 10 days, due to the long incubation time required to grow detectable *Legionella*. Thus, definitive confirmation of viable *Legionella* takes about ten days when using the Standard Method for detection. During this period, *Legionella* would have multiplied and spread in situ and at many instances the facilities may have to be shut down, resulting in production delays or limited occupation or evacuation and therefore, substantial economic losses. If detected earlier, and corrective measures taken earlier, economic loss may be minimized. According to OSHA specifications, a site may be considered potentially dangerously contaminated with *Legionella* bacteria if at least 10 colony forming units (CFU)/ml of *Legionella* are present in a drinking water distribution system or 100 CFU/ml in a cooling water system. In humidifiers, even 1 CFU/ml is considered potentially dangerous according to these OSHA guidelines.

For the Standard Method, buffered charcoal yeast extract (BCYE) medium is used to grow and culture *Legionella*. Several refinements and improvements resulted in the currently preferred BCYE medium that is enriched with α-ketoglutarate (Edelstein BCYE-α medium) with or without selective antimicrobial agents and indicator dyes. This medium can be supplemented with bovine serum albumin. For example, *Legionella* MWY selective supplement media from Oxoid Limited (United Kingdom; product code SR0118) includes per 100 ml of the medium, glycine 0.3 g; polymyxin B 5,000 IU; anisomycin 8.0 mg; vancomycin 100 µg; bromothymol blue 1.0 mg; and bromocresol purple 1.0 mg.

The Standard Method, as disclosed in the 1998 publication entitled "Water Quality Detection and Enumeration of *Legionella*", by the International Organization for Standardization of Geneva, Switzerland, which is commonly referred to as the ISO 11731 standard, specifies use of the BCYE-α medium supplemented with ammonia-free glycine, vancomycin, polymyxin B, and cycloheximide (GVPC). In addition to these supplements, GVPC or BCYE contains ferric pyrophosphate, L-cysteine, and as indicated, α-ketoglutarate. This method is generally consistent with the original method developed by the Centers for Disease Control and Prevention and with standard methods used in Australia and Singapore.

A method that is substantially similar to these is used in France (AFNOR T90431). In Standard Methods, selectivity steps such as acid treatment and/or heat treatment are required to inhibit competition from faster growing bacteria that may overwhelm *Legionella* in the sample.

The Standard Method requires a protocol for obtaining the samples, shipping them back to an analytical laboratory, and utilizes a specialized medium. In the laboratory, the method requires spreading a small volume of sample (0.1 ml) onto the surface of buffered charcoal yeast extract agar supplemented with growth factors and antibiotics and then incubating the media and the sample at a constant temperature and humidity for up to 10 days. The long incubation time is necessary because *Legionella* bacteria grow slowly on this growth medium. Growth on the agar surface must be sufficient for a microbiologist to count the number of colony forming units (CFU) on the surface of the agar after about ten days of incubation. The CFU count is used to determine a viable cell concentration by computing the value per unit volume. For example, a plate with 10 CFUs from 0.1 ml of undiluted sample indicates a viable *Legionella* concentration of 100 CFU/ml sample.

Several factors, however, limit the use of the Standard Method culture. First, an analyst's experience with the Standard Method directly correlates with pathogen quantification. Second, the Standard Method requires ten days to yield confirmed results, owing to the slow growth of *Legionella* on agar plates and the required confirmation tests. Third, the preparation of the medium is error-prone and requires extensive quality control. Fourth, the pathogen is sensitive to factors that are difficult to control during sample transit. Fifth, the concentration steps used to achieve lower detection limits are inefficient and not always reliable e.g., less than 50% of viable *Legionella* is recovered during sample concentration processing. Sixth, the method requires growing the pathogen to an extent that produces many visible colonies each containing millions or billions of potentially infective diseasecausing bacteria on the surface of the agar plates. This operation is dangerous and must be therefore performed by specially trained analysts in properly equipped laboratories to ensure the safety of the analysts and the surrounding community.

Other methods that are used, in addition to the above-described Standard Method, are molecular methods. Molecular methods are faster, less expensive, less subjective, more sensitive, and are capable of being performed in the field. However, they all suffer two critical limitations—none of the molecular methods, commercially available or otherwise, are able to 1) differentiate between viable, i.e., *Legionella* cells that can grow and be quantified under the conditions (media, incubation temperature) specified in the Standard Method, and the background of non-viable, or dead *Legionella* and 2) no quantitative determination of *Legionella* cells per unit volume (such as milliliters or liters) can be rendered from the data. Thus, in practice, only the above-mentioned Standard Method is able to detect the effect of disinfection of a contaminated or suspected site, because it is the only method that is capable of distinguishing between viable and non-viable *Legionella* bacteria and quantifying the hazard. Such differential and quantifiable detection is an essential requirement to confirm effective hazard control in engineered water systems. However, quantitative differentiation of viable *Legionella* is not a requirement in most clinical applications.

Molecular methods of *Legionella* detection include nucleic acid detection using the polymerase chain reaction (PCR) or fluorescence in situ hybridization (FISH), and serologic methods by antigen/antibody reactions detected with enzyme linked immuno-specific assays (ELISA) or differential fluorescent antibody direct cell counting. These molecular detection systems are useful in the clinical laboratory for diagnosis and sero-grouping *Legionella*. However, for environmental or industrial samples, nucleic acid or serological methods should be used only as a rapid screen to identify those samples that are completely free of any *Legionella* and not as a basis to detect or quantify viable and culturable *Legionella*.

Some of the distinguishing attributes of the Standard Method are: 1) differentiating viable from non-viable *Legionella;* 2) measuring all culturable species and sero-groups of *Legionella;* 3) providing a viable *Legionella* count that can be expressed per unit volume or weight of sample; 4) global recognition of validity.

Some of the severe limitations of the Standard Method are: 1) a long incubation period of ten days is required before CFUs can be visually counted because *Legionella* grow slowly on solid media; 2) storing agar plates for ten days during incubation requires significant incubator space and humidity controlled conditions; 3) the systems, such as cooling water, domestic water, soils, and the like from which samples have been taken, usually change very significantly during the ten day incubation period; 4) the act of growing biological hazards taken from the environment into visible colonies comprised of millions or billions more infective viable bacteria is dangerous and must be performed therefore, in a laboratory with trained persons and special equipment.; and 5) shutting down production in a facility contaminated or suspected to be contaminated with *Legionella*, closing the facility or restricting access to it for 10 days while waiting for confirmation that the biological hazard has been controlled results in significant economic loss. There are many examples of highly significant economic losses from such facility closures or restrictions.

A rapid detection system for *Legionella* that can quantify viable *Legionella* in viability units that are equivalent to those used in the Standard Method and is also capable of being used safely in a field setting is therefore desirable.

SUMMARY

Methods and compositions described herein to detect and quantify viable and culturable *Legionella* include dip-slides that contain an absorbent medium for absorbing a liquid sample, e.g., water. The dip-slides and quantifying methods disclosed herein enable numerical estimation of viable and culturable *Legionella* within a few hours in the field, 1-2 days, or possibly longer depending on transit time if prepared dip-slides are shipped to laboratory for analysis, compared to the 10 days required by the Standard Method. Dip-slide based detection and quantification of *Legionella* (i) is a rapid procedure capable of being performed in the field either partially, then shipped back to laboratory for final analysis, or completely, if qualified personal are available in the field; (ii) does not require sophisticated laboratory equipment such as microscopes or special protective equipment; (iii) is safe and (iv) can be performed without highly trained specialists such as microbiologists in the field. Methods used to complete analysis of the dipslides in the field or in the lab include polymerase chain reaction assays, differential fluorescent antibody assays, enzyme-linked immunosorbent assays, latex agglutination assays and fluorescence in-situ hybridization assays.

Devices disclosed herein support the growth and detection of microcolony forming units (MFU) within hours, thereby enabling early detection and quantification. Earlier detection of the microcolonies by the methods and compositions disclosed herein, minimizes the *Legionella* contamination, reduces economic loss due to possible longer shutdown of work facilities, and enables faster decontamination procedures.

In another aspect, a "Most Probable Number" (MPN) method to quantitatively determine viable *Legionella* is used, which is an analytical method to rapidly (within hours) determine the presence and quantity of viable *Legionella* bacteria.

The term "viable" as used herein means capable of multiplying and capable of being cultured under the growth conditions provided herein or in a medium capable of supporting the growth of *Legionella*. Viable cells form colonies on solid growth medium. The term "culturable" means that the microorganism is capable of being grown in the growth medium provided herein or in a medium capable of supporting the growth of *Legionella*.

The term "dip-slide" or "paddle" or "dip-slide sampler" or "paddle sampler" or "dip-slide tester" means a device that includes a solid support, an absorbent medium, and growth promoting substances for microorganisms, assembled in a slide-like or a paddle-like configuration for easy handling and storage.

The term "Standard Method" as used herein refers to a standard *Legionella* detection and quantification method as published by the International Organization for Standardization of Geneva, Switzerland, which is commonly referred to as the ISO 1731 standard and substantially similar methods such as the French AFNOR method, the AU/NZ standard and the CDC method. The Standard Method requires about 10 days for incubation and quantification of *Legionella*.

The term "absorbent medium" refers to any solid, semi-solid, gel, polymer, matrix, membrane layer or structure that is capable of absorbing or adsorbing or receiving or holding a specified amount of biological sample.

The term "microcolony forming units" (MFU) refers to a small aggregate of bacterial cells (less than 0.01% the number of bacterial cells in a visible colony) that is rendered visible upon magnification of about 2 times to about 10 times. Size of the microcolonies range from a few microns in diameter to about 500 microns in diameter. A normal bacterial colony may be 0.5 mm up to 10 mm or 15 mm in diameter and generally contain millions or billions of bacteria. A microcolony is smaller and generally contains a few hundreds or thousands of bacteria. Microcolonies are observed directly or with the magnification generally available with a digital camera (2×-10×) on the surface of dip-slides after about 24 hrs to 44 hrs and with the aid of detection agents and imaging methods disclosed herein, detection of *Legionella* microcolonies are achieved in a few hours, e.g., about 6-8 hours.

The term "detection reagent" refers to any agent that is capable of selectively identifying *Legionella*.

A method of rapidly quantifying viable *Legionella* bacteria in a sample includes the steps of:
(a) providing a dip-slide comprising an absorbent medium, wherein the absorbent medium includes nutrients for culturing *Legionella* and at least one agent to selectively inhibit the growth of non-*Legionella* microorganisms;
(b) contacting the dip-slide with the sample for a predetermined amount of time, wherein the dip-slide is calibrated to absorb a predetermined amount of the sample;
(c) incubating the dip-slide at a temperature in the range of 30° C. to about 45° C. for a period sufficient to exhibit microcolonies, periods which range from about 6 hours to about 48 hours, possibly 72 hours, but much less than 10 days; incubation is occurring during transit if analysis is done in a laboratory;
(d) detecting growth of *Legionella* bacteria on the dip-slide with a detection reagent, wherein the detection agent selectively identifies *Legionella*; and
(e) quantifying the amount of viable *Legionella* bacteria in the sample.

The absorbent medium comprises agarose in a range of about 0.5 wt % to about 10.0 wt %. The detection reagent is selected from the group consisting of an antibody, a mixture of antibodies, a probe, and combinations thereof The antibody is specific for *Legionella* selected from a group that includes *Legionella pneumophila* serogroups 1-13, *L. longbeachae, L. bozemanii, L. micdadei, L. dumofffii, L. feeleii, L. wadsworthii*, and *L. anisa* and other species, subgroups, and serogroups of *Legionella.*

The probe is selected from a group that includes a dye, a color enhancing dye, a phase contrast dye, a labeled probe, a fluorescent probe, a calorimetric probe, a nucleic acid probe, and combinations thereof The detection of *Legionella* is by an ultraviolet light source.

The absorbent medium is calibrated to absorb about 0.3 ml of the sample in about 60 seconds. The detection reagent increases contrast for imaging the growth of *Legionella*. The detection reagent kills *Legionella*. The detection reagent includes an antimicrobial compound selected from a group that includes isothiazolone, glutaraldehyde, formaldehyde, ammonium quaternary compounds, dibromonnitrilopropionamide, beta-bromonitrostyrene, carbamate antimicrobials, tris-nitromethane antimicrobials, sodium benzoate, organic acids, ethanol, isopropanol, chlorhexidine gluconate, chlorhexidine diacetate, o-phenyl phenol and any suitable antimicrobial compound.

An agent to selectively inhibit the growth of non-*Legionella* microorganisms includes dyes, glycine, vancomycin, and polymyxin (DGVP) and/or an inorganic or an organic acid. An agent to selectively inhibit the growth of non-*Legionella* microorganisms includes cephalothin, colistin, vancomycin and cycloheximide (CCVC).

The growth of *Legionella* is detected as a microcolony, wherein the microcolony is about 10-500 microns in diameter. The growth of *Legionella* is detected as a microcolony under a magnification in the order of about 2× to about 10×.

A dip-slide detection system for rapidly quantifying viable *Legionella* bacteria in a sample includes:

(a) a dip-slide that includes an absorbent medium, wherein the absorbent medium includes nutrients for culturing *Legionella*, at least one agent to selectively inhibit the growth of non-*Legionella* microorganisms, wherein the dip-slide is adapted to absorb a predetermined amount of the sample; and (b) a detection reagent to quantify the amount of viable *Legionella* bacteria in the sample, wherein the detection reagent inhibits the growth of *Legionella.*

A dip-slide for rapidly quantifying viable *Legionella* bacteria in a sample, includes an absorbent medium, nutrients for *Legionella* bacteria, at least one agent to selectively inhibit the growth of non-*Legionella* microorganisms, wherein the dip-slide is adapted to absorb a predetermined amount of the sample.

A method of rapidly quantifying viable *Legionella* bacteria in a sample includes the steps of:

(a) providing a liquid growth medium for *Legionella* bacteria containing growth preventing substances for non-*Legionella* bacteria;

(b) performing serial dilutions of the sample, wherein the serial dilutions are designed to result in a dilution that does not contain a *Legionella* bacterium;

(c) incubating the serial dilutions at a temperature in the range of 30° C. to about 45° C. for a period of about 6-8 hours to about 44 hours;

(d) detecting the presence of *Legionella* growth in the serial dilutions with a detection agent; and (e) applying a most probable number (MPN) statistical method to quantify the amount of viable *Legionella* bacteria present in the sample.

There are 15 serogroups of *L. pneumophila* and about 70 serogroups in total for *Legionella*. Some of the *Legionella* isolates and serogroups that cause infection include *L. longbeachae, L. bozemanii, L. micdadei, L. dumoffii, L. feeleii, L. wadsworthii*, and *L. anisa*. Two other genera have been proposed: *Fluoribacter* blue-white fluorescing species such as *L. bozemanii* and *Tatlockia* for the species *L. micdadei*. Phylogenetically close relatives of *Legionella* can also be detected and quantified using the methods disclosed herein.

The disclosed methods provide practical and effective improvements over the Standard Method acid pretreatment; provides a way to use field samplers for the total heterotrophic aerobic bacterial count in addition to viable *Legionella*; provides a method to simplify and expedite obtaining analytical results and interpretations of data by shipping processed field samplers back to the lab and provides a way to entirely eliminate the variability which occurs in the Standard Method resulting from shipping water samples back to the laboratory before analysis can occur.

Various new and improved means were found to accomplish the acid pretreatment of samples in the field to inhibit non-*Legionellae* bacteria. The Standard Method requires use of an HCl buffer solution to acidify the sample. The purpose of the acid pretreatment step required in the Standard Method is to inhibit growth on the media of common aquatic bacteria found in water samples; such bacteria are much more sensitive to acid pH environments compared to the *Legionellae* which are tolerant to acidic pH. By means of this acid pretreatment, many rapidly growing bacteria such as *Pseudomonas* and *Flavobacterium*, for example, are completely inhibited from growing on BCYE therefore, allowing for growth of the slower growing, pH tolerant *Legionella*. In place of the HCl buffer, organic acids including ascorbic acid, glycine and cysteine provide equivalent results to the standard method acid pretreatment requirement. In the field it is preferable to use solid organic acids rather than HCl because the solid organic acids are safer and more convenient to handle. Additionally, since *Legionella* require cysteine for growth, use of the cysteine-HCl salt for acid pretreatment of the sample is especially useful. Absorbic acid with glycine and cysteine is suitable. The quantity of acid added to the sample can be from 0.01 g to 5 g.

A dip-slide without acid pretreatment is used to provide estimates of total heterotrophic bacteria. The total number of colonies can be counted or compared to charts of known colony concentrations to estimate the total aerobic heterotrophic bacteria. Also, by subtracting the number of microcolonies of *Legionella* growing on the dip-slide with acid pretreatment, from the number of microcolonies on the non-acid dip-slide, the heterotrophic bacteria excluding *Legionella*, can be determined.

An added benefit is that no dilution of the sample is needed. In the Standard Method, the sample is diluted 1 part sample to 1 part HCl buffer solution. In the method disclosed herein, just enough solid organic acid is added to achieve the necessary pH (~2.2) without diluting the sample. This is preferred because sample dilution reduces the limit of sensitivity for the assay. For example, the limit of sensitivity for the assay is 10 CFU/ml but since the sample is diluted 1:2 in the Standard Method, the actual limit is 20CFU/ml. With the improved method, no dilution is necessary because the solid organic acid which is added also immediately dissolves into the sample.

The quantity of acid added to the sample can be from 0.01 g to 5 g.

Absorbic acid and two amino acids (glycine and cysteine) are suitable.

Surprisingly, the *Legionella* field sampler is useful to determine the total heterotrophic aerobic bacteria even more accurately than other field methods available today. It is useful to analyze viable *Legionella* and also the viable total heterotrophic aerobic bacterial count. The field method surprisingly allows determinations BOTH of these important parameters simultaneously for each water sample analyzed by the methods described.

Processing the field samples in the field using the acid pretreatment and then shipping them back to the laboratory for data archiving and interpretations provides the following benefits:

a) allows acid pretreatment without sample dilution;
b) utilizes the time in transit as incubation period for the field samplers;
c) eliminates variation in the Standard Method due to transit time of water samples during which microorganisms increase or decrease depending upon unpredictable factors in the water sample itself, and
d) provides a convenient, cost-effective and sustainable process for interpreting and archiving the data from field samples processed in the field.

BRIEF DESCRIPTION OF THE DRAWINGS

The drawings are provided to illustrate some of the embodiments of the disclosure. It is envisioned that alternate configurations of the embodiments of the present disclosure are within the scope of the disclosure.

FIG. 1 shows the surface of a *Legionella* dip-slide used for the rapid determination of viable cell concentrations in water samples. This slide was dipped for 60 seconds into about 1000 CFU/ml viable cell suspension (sterile 0.1M KCl) of *Legionella pneumophila* ATCC 33152. Weight increase after 60s dip was about 0.3 g. The volume of sample absorbed was therefore, about 0.3 ml. The dip-slide was incubated at 35° C. for about 45 hours. Digital photographs were printed with 0% color saturation, maximum contrast and by adjusting adjust brightness more (B) or less (A). Nearly actual size of the dip-slides is shown. Microcolony forming units (MFU) are shown as indicated by arrows.

FIG. 2 shows a paddle sampler (B) and container (A) as part of the dip-slide assembly.

FIG. 3 shows total heterotrophic aerobic bacterial growth and enumeration on dip-slides.

FIG. 3A shows Biosan* Sani-Check® Comparator is a commercially available dipslide used for quantitative determination of total heterotrophic bacterial in water samples.

FIG. 3B shows Biosan Sani-Check® results of real-world samples confirming that the Biosan sampler is accurate.

FIG. 3C demonstrates that The Phigenics Validation Test® (PVT) described and claimed herein is shown to be equally accurate and convenient compared to the Biosan comparator (FIGS. 3A and 3B). These results were surprising because the growth media used for PVT has not been previously used for total counts and because no colony-enhancing dyes (such as are used in the Biosan sampler) were necessary for easy and convenient enumeration of bacterial colonies.

DETAILED DESCRIPTION

A rapid analytical field method and system are provided that utilizes a rapid dip-slide. The rapid dip-slide method to quantitatively determine viable *Legionella* is an analytical method to rapidly (within hours) determine the presence and quantity of viable *Legionella* bacteria. Viable *Legionella* can be enumerated the same day that the sample is taken. Unlike the standard method, the methods and devices disclosed herein are performed in the field at the site where the sample is taken either partially with analysis being completed in a laboratory or completely in the field. Results, which are statistically equivalent to those obtained with the Standard Method, are available the same day the sample is taken in the field and not shipped to a lab or within 1-2 days, or possibly longer but still much less than 10 days depending on transit time of dip-slides to be analyzed in a laboratory. Preparation of a dip-slides in the field removes the problems associated with shipping water samples, requirements for special reagents or instruments to interpret the results.

A dip-slide is prepared as follows. The standard BCYE media is prepared with modifications to make it suitable for use in the dip-slide format. The modifications of media are provided herein.

Preparation of absorbent medium involves the use of agarose or any suitable absorbent medium. Compared to the standard method, about 0.5-10% more agarose is used to prepare the absorbent medium for dip-slides used herein. For example, 1.3% agarose is calibrated to absorb about 0.3 ml or 0.3 g of the sample in about 60 seconds. Increasing the agarose concentration results in lower amount of the sample being absorbed. Depending on the requirements, 0.5 to about 10% agarose concentration can be used to calibrate the absorbent medium. For example, by adjusting the agarose concentration, about 0.1 ml of the sample is absorbed within a pre-determined amount of time, e.g., 1 min. The user can also be instructed to vary the dipping time instead of varying the concentration of agarose. For example, by keeping the concentration of agarose constant at 1.5%, the dip-slides can be dipped for a period of about 30 seconds to about 2.0 minutes depending on sample quality, bacterial count, and sample volume. In an experiment to quantify viable *Legionella*, a number of dip-slides can be dipped in the sample for a varying amount of time and compared. In an aspect, the concentration of agarose can range from about 0.2% to about 5.0%. Agarose concentration may also range from about 0.8% to about 1.6% and from about 1.0% to about 2.0%. The lowest possible concentration of agarose or any suitable polymer or gelling material that can be used on a dip-slide depends on the stability of the resulting polymerized absorbent medium and its ability to be retained in the dip-slide assembly during sampling handling steps. An absorbent medium capable of supporting bacterial growth in a dip-slide is within the scope of the disclosure.

During the preparation of absorbent medium, growth promoting substances are incorporated. Growth promoting substances for *Legionella* include the components of buffered charcoal yeast extract (BCYE) medium. The BCYE medium is enriched with α-ketoglutarate (Edelstein BCYE-α medium) and other growth promoting amino acids and metabolites can be incorporated to selectively enhance the growth of *Legionella*. A growth medium that supports the growth of *Legionella* is within the scope of this disclosure. The growth medium can be supplemented with one or more amino acids, micro and macro nutrients, and selective supplements. For example, *Legionella* MWY selective supplement media from Oxoid Limited (United Kingdom; product code SRO 118) includes per 100 ml of the medium, glycine 0.3 g; polymyxin B 5,000 IU; anisomycin 8.0 mg; vancomycin 100 μg; bromothymol blue 1.0 mg; and bromocresol purple 1.0 mg.

During the preparation of the absorbent medium, in an aspect, growth selective substances such as antibiotics can be incorporated. Growth selective substances, such as acid-releasing compounds and antibiotics to prevent growth of non-*Legionella* microorganisms are incorporated in the absorbent medium. These compounds can also be added after the absorbent medium is made.

Incorporation of calorimetric indicators such as a *Legionella* antigen system used in the molecular immunological antibody/antigen systems or the fluorescent antibody such as that used in the FISH system aid and enhance early detection and quantification of *Legionella*. Some of the indicators can be directly incorporated in the absorbent medium itself or can be added later during the detection step as a separate reagent. *Legionella* specific antibody reagent is added directly to the dip-slide surface followed by labeled detection reagents. For example, rabbit or mouse anti-*Legionella* polyclonal antibody conjugated to horse radish peroxidase enzyme is added to the surface of the dip-slides after slides with the sample were incubated for about 6-10 hours or to about 40 hours. After the antibodies are bound to the *Legionella* specific proteins, a chromogenic substrate such as TMB is added to detect the antigen-antibody binding. TMB is a chromogen that yields a blue color when oxidized with hydrogen peroxide (catalyzed by HRP) with major absorbances at 370 nm and 652 nm (Pierce Biotechnology, Inc., Rockford, Ill.). The color then changes to yellow with the addition of sulfuric or phosphoric acid with maximum absorbance at 450 nm. The antigen-antibody binding analysis described herein can also be performed on nylon or nitrocellulose membranes that contain the bacterial colonies. The membranes are used to lift off the bacterial colonies (see Example 4) and the procedures described herein are applicable to detect and quantify *Legionella* transferred to the membranes.

This same approach is highly useful when the antibodies are monoclonal antibodies to epitopes of stains known to be associated with severe outbreaks of legionellosis such as Mab2, from the CDC.

In an aspect, DNA probes can also be used to detect and quantify *Legionella*. For example fluorescently labeled DNA probes that are specific or complementary to a unique region of *Legionella* DNA are useful to practice fluorescent in situ hybridization (FISH). FISH can be practiced either directly on the surface of the dip-slides or on the membranes to which the colonies have been transferred. A cell permeabilizing and immobilization agent can be used to fix the bacterial microcolonies on to the agarose surface or on the membranes before the application of the fluorescent probes. The fluorescently labeled probes can be visualized under UV or other appropriate light source.

In an aspect, growth inhibiting substances such as antimicrobials, biocides, bactericidal, anti-bacterial agents are included in the detection reagent to simultaneously detect and inhibit further growth of *Legionella*, thereby minimizing contamination. For example, antimicrobial isothiazolone (Rohm and Haas, Philadelphia, Pa.) is a suitable growth inhibiting substance that can be added either during the detection phase or after the detection phase for the purpose of completely killing the microcolonies of pathogenic bacteria so that the device can be discarded safely.

The dip-slides disclosed herein can be used as follows: a water sample is obtained using aseptic technique. The dip-slide is removed from the cover and is immersed into the sample for about 30-60 seconds depending upon the dip-slide and the sample. The dip-slide is placed into the cover and is incubated for about four to forty hours at about 30° C. After about four hours to forty hours, a few hundred to thousands of cells are grown on the surface of the agar. This bacterial amount is far too small to see without the aid of sophisticated magnification equipment unless treated by the methods disclosed herein. These microcolonies, which contain less than about 0.01% the number of pathogens that would be required to count them in the Standard Method, are visualized without a microscope with a digital camera, and/or with the aid of detection reagent or a combination of these methods as disclosed herein. The microcolonies or microcolony forming units (MFU) are counted on the surface of the dip-slide and the data are stored as a digital image for future reference.

There are at least five types of developing agents that are suitable for detection and quantification of *Legionella* on dip-slides. A solution of the antibody used to detect Lp antigen of *Legionella* is suitable. Colorimetric detection system used in the urine antigen test may be used (Binax, Inc., Scarborough, Me.). In addition, an antigen-antibody system, where the antibody is capable of reacting with several species and serotypes of *Legionella* are used. A hand-held UV diode or mercury lamp, for example, is used to illuminate the surface of the dip-slide in order to visualize the microcolonies of *Legionella*. The reagent system used in the FISH (fluorescent in situ hybridization) system is suitable for detecting *Legionella* on the dip-slide disclosed herein (Vermicon AG, Munich, Germany). A simple biomass calorimetric system for visualizing the presence of microcolonies on the surface of the dip-slide, such as spraying the surface with ninhydrin to react with proteins or a vital stain like methylene blue to react with biomass is also suitable.

As described herein, the dip-slide method may also use a "replica blot"—by gently placing a sterile piece of filter paper or membrane on the dip-slide surface, and then carefully peeling it away and taking with it the cells that have multiplied into microcolonies on the dip-slide surface. The filter paper or the membrane replica is developed with the reagents disclosed herein. The replica blot may remove background interference from the contents of the media such as those that may exist in BCYE agar. In another aspect, this method may require a "replica slide"—by gently placing a sterile piece of glass with surface area dimensions equal to the surface area of the dip-slide onto the dip-slide for a period of about one second and then removing the slide. The biomass from microcolonies on the dip-slide will adhere to the glass surface. The biomass is then "heat fixed" by holding an open flame under the glass for about 1 sec. The heat-fixed proteins, carbohydrates, and lipids adherent to the slide can now be detected with the detection systems disclosed herein.

A membrane replica is not needed when the detection and quantification are performed on the surface of the dip-slide directly. For example, a user in the field, after a period of incubation of about 6-8 hours, dips the slide in a reagent solution that may have a suitable detection agent such as a *Legionella* specific antibody or a nucleic acid probe or a color-enhancing agent. The dip-slide is exposed to the reagent for a few minutes to a few hours. The reagent may also have a bactericidal agent that kills or inhibits the growth of *Legionella*. The dip-slide is then viewed either directly with the naked eye or with help of magnification equipment such as the digital or optical zoom of a digital camera. A digital image is captured at 2×-10× magnification and quantified by counting the microcolony forming units.

The number of detected microcolonies on the surface of the *Legionella* dip-slide is used to estimate the number of viable cells per ml of sample depending on how the agar is calibrated to absorb a pre-determined amount of sample. For example, if there appears 100 microcolony forming units (MFU) after 10 hours of incubation on the surface of a dip-slide that had an agar concentration of 1.3 wt % and was dipped for 60 seconds, then about 0.3 ml of the sample would have been absorbed and therefore the colony count per ml is about 333.

*Legionella* is grown directly on top of a membrane (e.g., nitrocellulose), wherein the membrane strip is placed on top of an agar layer for absorption of nutrients. The membrane strip is directly used for further detection as disclosed herein. Some of the detection reagents (e.g., TMB) are incorporated within the agarose itself for later detection.

The rapid-analytical *Legionella* detection system may also utilize a "most probable number" (MPN) method to quantitatively determine viable *Legionella*. This method is an analytical method to rapidly (within hours) determine the presence and quantity of viable *Legionella* bacteria. Viable *Legionella* can be enumerated the same day that the sample is taken. The MPN technique is a statistical method and has been used to enumerate viable bacteria (prokaryotes) in samples of water, air, food, and other substances. Briefly, MPN method involves the use of serial dilutions performed in replicates of 3 or 5 or 7. Tubes are filled with 9 mL of sterile medium and inoculated with either sediment slurry or directly with sediment using a 5-mL syringe. The ten-fold dilutions are done through three to six steps, sufficient that the last dilutions would probably not contain growing prokaryotes. The tubes showing positive growth by becoming turbid after an incubation are recorded and used to calculate the most probable number of viable cells in the original sample, according to a conventional statistical table based on the probability function.

No field MPN method has been devised for *Legionella* quantification. Most Probable Number (MPN) methods are used in food microbiology and sanitation applications. Conventional detection of *Legionella* by standard MPN methods make take several days due to the slow growth of *Legionella*. The methods disclosed herein enhance the speed with which MPN is useful for enumerating bacterial count within a few hours to about 2 days.

One example of the MPN-based detection method is as follows. Standard liquid media for *Legionella* is prepared as follows—5 g bovine serum albumin, fraction V; 10 g N-2-acetamido-2-amsinoethanesulfonic acid (ACES); 10 g yeast extract; 0.4 g L-cysteine-HCl; 0.25 g soluble ferric pyrophosphate were dissolved in 800 ml of distilled and the pH was adjusted to pH 6.9 with 1 N potassium hydroxide. The solution was filter sterilized and stored at 4° C. for up to six months, protecting from light exposure. A stock solution can me made that has up to 3× strength and diluted as needed later. Modifications of the standard media described herein include incorporation of growth accelerating substances such as more nutrient; incorporation of calorimetric indicators such as the *Legionella* antigen system or the fluorescent antibody indicators; and use of a detection system such as a developing reagent for the antigen or a handheld UV-diode illuminator to indicate presence of microscopic colonies.

An example of the MPN method includes the following steps—a water sample is obtained; the sample is inoculated in triplicates; the samples are serially diluted in triplicates. Four more dilutions are performed in triplicates. After about 4-8 hours a few hundred to thousands of cells would have grown in the positive tubes. Generally, this number is too low to result in a visible turbidity to the naked eye. However, by using detection and visualization agents disclosed herein, the few hundred to thousands of cells in positive tubes are visualized. As disclosed herein there are several types of detection agents that are suitable for visualizing *Legionella*. These include antibody reagents, calorimetric detection system, a hand-held UV diode lamp, FISH (fluorescent in situ hybridization) system, and a protein detection system such as ninhydrin or a vital stain like methylene blue to react with biomass.

This method may require syringe filtration. One cc of the sample from each tube is filtered through syringe tip filter. The filter paper is now developed with the reagents disclosed herein. The filtration step may remove background interference from the contents of the media.

The data is interpreted as follows—the pattern of positive tubes in the series is used to calculate the "most probable number" (MPN) of viable cells in the sample. The calculation is based on the probability function. MPN calculators are available and are known to those of ordinary skill in the art. The MPN value is substantially equivalent to the information reported from the Standard Method as CFU *Legionella* spp/ml.

Method and compositions disclosed herein detect several serogroups and isolates of *Legionella* including *Legionella adelaidensis, Legionella anisa, Legionella beliardensis, Legionella birminghamensis, Legionella bozemanae, Legionella bozemanii, Legionella brunensis, Legionella busanensis, Legionella cherrii, Legionella pneumophila, Legionella pneumophila* subsp. *fraseri, Legionella pneumophila* subsp. *pascullei, Legionella pneumophila* subsp. *pneumophila, Legionella rowbothamii, Legionella taurinensis, Legionella worsleiensis*, and *Legionella nautarum.*

While specific embodiments of the invention have been shown and described, it is to be understood that numerous changes and modifications may be made therein without departing from the scope and spirit of the invention.

EXAMPLES

The following examples are for illustration only and do not in any way limit the scope of this disclosure.

Example 1

This example demonstrated that the methods and compositions disclosed herein to detect viable and culturable Legionella, improves by at least 80%, the time required to quantitatively determine viable Legionella in water samples by standard method.

DuPage River water was sampled in Naperville, Ill. To the river water sample, a Quantity of Legionella pneumophila (ATCC 33152) was added aseptically. The inoculated river water was then mixed and allowed to equilibrate. Aliquots of the sample were placed onto the growth medium with final dilutions of 1:10, 1:100 and 1:1000 in sterile phosphate buffered saline. The experiment was replicated twice. Viable cells were determined by counting "Microcolony Forming Units" (MFU) and Colony Forming Units (the Standard Method). The MFU can also be counted by naked eye from digitally enlarged images (10× zoom). Microcolonies of *Legionella pneumophila* were enumerated after 42 hrs, 65 hrs and 93 hrs of incubation at 35° C. Colonies of *Legionella pneumophila* were enumerated by the Standard Method after 10 days of incubation at 35° C. Table 1 shows the data and the results of statistical analysis. The number of Microcolony Forming Units per milliliter of water sampled (MFU/ml) was not statistically different than the number of Colony Forming Units per milliliter of water sampled (CFU/ml) after 10 days as required by the Standard Method. Therefore, detection of MFU by the rapid method disclosed herein is an equivalent analytical method to the long and laborious Standard Method.

Table 1 shows the number of viable *Legionella pneumophila* in river water as determined by the rapid method disclosed herein compared to the 10 day count with the Standard Method. There was no statistically significant difference in the bacterial numbers at day 10 and the numbers from analyses performed at earlier times. These data show that the data obtained at 42 hours was equivalent to the data obtained after 10 days. This represents an 83% improvement in the time required to obtain the viable cell concentration of *Legionella* in river water.

TABLE 1

Comparison of *Legionella* detection by a rapid method compared to the Standard Method results at 10 days incubation.

| Time | MFU or CFU Counted | MFU or CFU Counted | Ave | SD | Average MFU/ml or CFU/ml | SD/ml |
|---|---|---|---|---|---|---|
| | | | Trial 1 | | | |
| 42 h | 60 (MFU) | 23 (MFU) | 41.5 (MFU) | 26.2 | 6.9E+05 | 4.4E+05 |
| 65.5 h | 70 (MFU) | 40 (MFU) | 55 (MFU) | 21.2 | 9.2E+05 | 3.5E+05 |
| 93 h | 66 (MFU) | 52 (MFU) | 59 (MFU) | 9.9 | 9.8E+05 | 1.6E+05 |
| 10 days | 67 (CFU) | 50 (CFU) | 58.5 (CFU) | 12.0 | 9.8E+05 | 2.0E+05 |
| | | | Trial 2 | | | |
| 42 h | 100 (MFU) | 72 (MFU) | 86 (MFU) | 19.8 | 1.4E+06 | 3.3E+05 |
| 65.5 h | 105 (MFU) | 83 (MFU) | 94 (MFU) | 15.6 | 1.6E+06 | 2.6E+05 |
| 93 h | 108 (MFU) | 78 (MFU) | 93 (MFU) | 21.2 | 1.6E+06 | 3.5E+05 |
| 10 days | 105 (CFU) | 74 (CFU) | 89.5 (CFU) | 21.9 | 1.5E+06 | 3.7E+05 |

MFU—microcolony forming units;

CFU—colony forming units observed in the Standard Method at Day 10

SD—Standard deviation

Compositions and methods disclosed herein enable detection of viable, culturable *Legionella* that is comparable to the Standard Method. Unlike the Standard Method, the rapid method disclosed herein enables detection within a few hours.

Example 2

This example demonstrates that the dip-slides and methods disclosed herein are useful in quantifying *Legionella* bacteria following a disinfection procedure. In an aspect, dip-slides for *Legionella pneumophila* were used to measure the effect of chlorine disinfection (Table 2, FIGS. 1A, B and 2). A BCYE/BCYE+DGVP dip-slide was weighed prior to the sample introduction. The dip-slide was dipped in the sample for about 60 seconds and the dip-slide was weighed again to insure about 0.3 g of the sample was adsorbed to the dip-slide. The sample-loaded dip-slide was incubated at 35° C. for about 45 hours. The dip-slides were taken out of the incubator and were photographed digitally.

If a water system, such as a drinking water distribution system or cooling water utility system, becomes contaminated with the *Legionella* hazard, then that system should be immediately disinfected. For example, the Occupational Health and Safety Administration (OSHA) has published guidance for procedure to be followed in response to results from quantitative analysis obtained from the Standard Method for viable *Legionella* concentrations (measured as Colony Forming Units per milliliter, CFU/ml) in water samples. These guidelines indicate, for example, that if the concentration of viable *Legionella* in drinking water is greater than 10 CFU/ml, then procedures should be followed to disinfect the water. To determine the extent and efficiency of detection, the disinfected water sample needs to be analyzed for any remaining *Legionella* bacteria.

However in order to determine the extent of the disinfection, 10 days are required in the Standard Method to obtain quantitative results. In many cases, a facility must be evacuated and closed until results from the Standard Method are available in order to ensure that disinfection has been adequate and that the building is safe for occupants and users. In some countries such as in France, it is a legal requirement that the water system should remain unused and the facility evacuated until there is quantitative proof that the disinfection has been effective.

Figure 2:
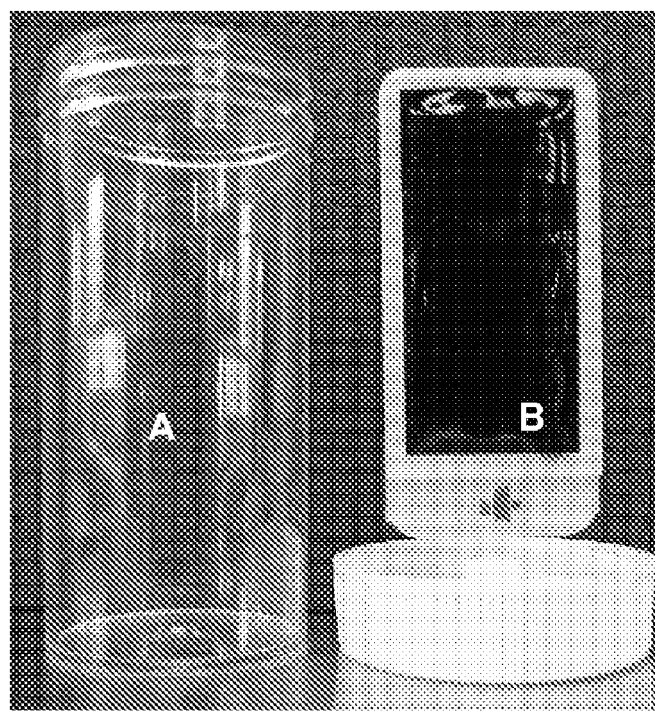
Figure 3:
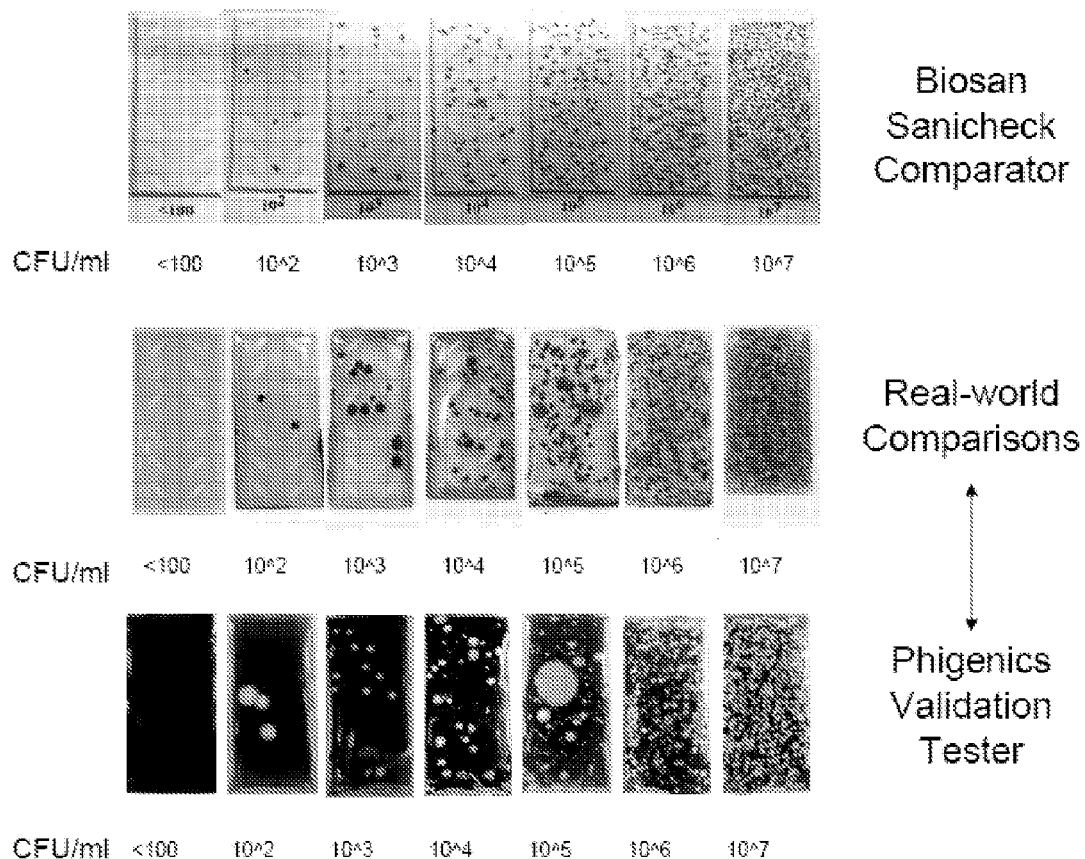
Figure 3A:
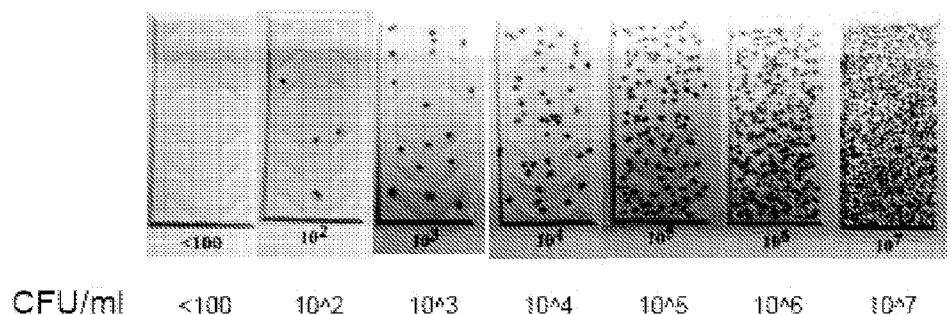
Figure 3B:
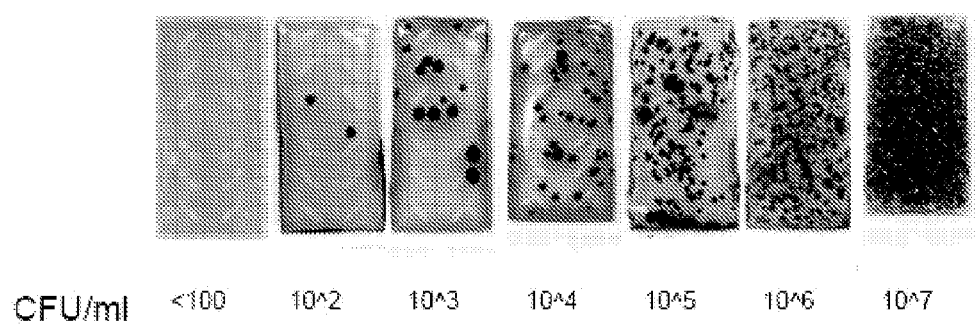
Figure 3C:
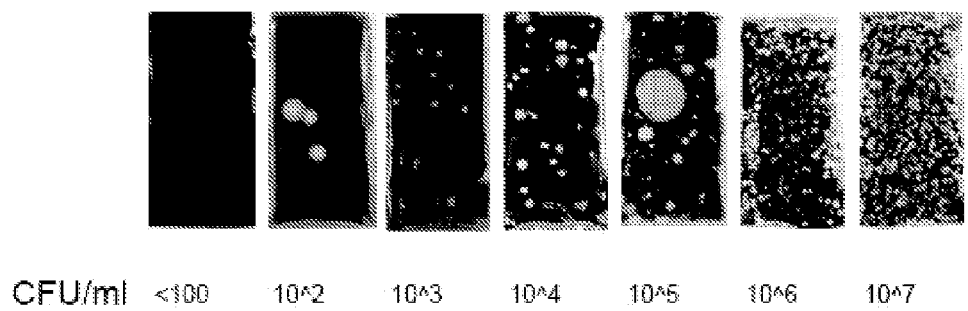

With the rapid dip-slide method disclosed herein, statistically equivalent data to the Standard Method can be obtained much faster (see Example 1,Table 1). The data in Table 2,FIGS. 1-2 show that effective disinfection was successfully observed, quantified and documented using the new Legionella dip-slides. These results provide quantitative assurance that the hazard (*Legionella* bacteria) has been controlled.

One hundred milliliter (ml) sample of water containing about 8-25 viable *Legionella* cells per ml was treated with a 0.17 mg/l free residual oxidant measured as $Cl_2$ with a calorimetric test using a HACH DR-890 hand-held calorimeter. Dip-slides were used to measure the viable *Legionella* concentration after 1, 5 and 10 min of contact with the chlorine disinfectant and compared to dip-slide results obtained from identically prepared (except no chlorine) untreated controls.

TABLE 2 demonstrates that effective disinfection was observed with the new *Legionella* dip-slides.

| | No Chlorine (Control) | | Chlorine* (Treatment) | | |
|---|---|---|---|---|---|
| Contact Time (min) | *Legionella pneumophila* (Ave MFU/dip-slide) | *Legionella pneumophila* (Ave MFU/ml) | *Legionella pneumophila* Ave (MFU/dip-slide) | *Legionella pneumophila* (Ave MFU/ml) | **% Disinfected |
| 1 | 4 | 12 | 3 | 8 | 33 |
| 5 | 8 | 25 | 0 | 0 | 100 |
| 10 | 3 | 8 | 0 | 0 | 100 |

MFU = microcolony forming unit; dip-slides were calibrated to absorb 0.3 ml of sample in a 30 s "dip" at room temperature
*Free residual oxidant concentration = 0.17 mg/l (ppm) as Cl2; Total residual oxidant concentration = 0.25 mg/l (ppm) as Cl2
**"% Disinfected" was calculated from MFU/ml measurements [(control − treatment)/control] × 100

Dip-slides and methods disclosed herein are used to detect and quantify *Legionella* from samples after a disinfection procedure to determine the efficiency of disinfection. Growth of *Legionella* may be influenced by the nature of the disinfection procedure.

Example 3

This example provides an illustration of a dip-slide and a dip-slide chamber in a dip-slide assembly for detection and quantification of *Legionella*.

Dip-slides illustrated in this example are also designated "paddle dip-slide samplers". These paddle dip-slides and chambers were fabricated in the dimensions as follows. Plastic paddles were 6 cm in length, 2.75 cm width and 0.5 cm depth (FIG. 2B). On both sides of the paddle sampler, a 4.75 cm×2.25 cm rectangle reservoir of 1 mm depth was made to hold the growth media and the absorbent material. The paddle was fitted into a threaded screw cap 4 cm in diameter which fit onto a threaded clear plastic tube, 7.5 cm in length (FIG. 2A). The paddle (dip-slide) and the reservoir constitute a dip-slide assembly. The entire assembly was sterilized by autoclave. On one side of the paddle, sterile standard media Buffered Charcoal Yeast Extract (BCYE) agar was aseptically poured into the reservoir. On the other side, sterile BCYE plus antibiotics (as specified in the Standard Method) was aseptically poured into the reservoir and the side with the antibiotics was identified with a distinguishing visual mark. FIG. 2 shows an illustration of the rapid method *Legionella* dip-slide sampler.

Paddle testers or dip-slide samplers with agar medium for bacteria other than *Legionella* are available from a variety of commercial suppliers, such as, for example, from Biosan Laboratories, Inc. (Warren, Mich.). Based on the guidance and the specifications of the growth medium, the absorbent medium, and reagents disclosed herein, dip-slides or paddle-testers for *Legionella* can be constructed.

Other suitable dimensions for dip-slides include for example, in one aspect, about 2-10 cm in length, 1.0-4.0 cm width and 0.1-1.0 cm depth and about 5 -15 cm length, 2-10 cm width, and 1.0-2.0 cm depth. Accordingly, suitable reservoirs to the dip-slides disclosed herein can have varying dimensions. For example, in one aspect, the reservoirs are dimensioned to be about a 2.0-10.0 cm×1.0-4.0 cmrectangle reservoir of 1-5 mm depth made to hold the growth media and the absorbent material. Containers or tubes to fit the dip-slide along with the reservoirs can also have varying dimensions. For example, in one aspect, the containers can be of cylinder of about 5-12 cm in length and appropriate diameter.

The dip-slides, the reservoirs, and the containers can be made of any suitable material, including but not limited to plastic, polymer, acrylic, and neoprene. The paddles or the dip-slides can also be any suitable shape, e.g., rectangle, oval, circular, and square.

Example 4

This example illustrates steps to selectively identify microcolonies of *Legionella* on the Dip-slide Sampler using a labeled anti-*Legionella* antibody.

Bacterial microcolonies (less than 2 day growth) on the surface of the rapid method *Legionella* dip-slide sampler, as disclosed herein, were transferred to a nitrocellulose membrane (0.22 micrometer pore size for Western blotting, Bio-Rad) by laying the membrane on the dip-slide for 1 minute. A substantial amount of the microcolonies were lifted and transferred to the membrane. The membrane was air dried for 20 minutes to fix the bacterial proteins to the membrane. The membrane was then soaked in 1% skim milk (Difco), 0.1% Tween 20 (Sigma) to block the remaining protein binding sites. The membrane was then cut in two, so that one half (Membrane "A") represented the upper part of the dip-slide used for specific detection. The other half (Membrane "B") was used for the control. The distribution of microcolonies (20 or so) was fairly uniform over the dip-slide.

Membrane A was transferred to a petri dish containing 3 ml of a 1/500 dilution of horseradish peroxidase labeled rabbit anti-*Legionella* (Accurate Chemical & Scientific Corporation, Westbury, N.Y.) in 1% skim milk, 0.1% Tween, in phosphate buffered saline (PBS). Membrane B (the control) was transferred to a similar dish containing rabbit anti-mouse IgG as a control. Membranes were gently agitated for 3 minutes then rinsed 5 times with PBS with 0.1% Tween. Five ml of TMB substrate chromogen for blotting was placed in a clean dish and the membranes were gently shaken for 5 minutes for color development. Development was stopped by a brief water rinse. Spots on the membrane where colonies had contacted the membrane appeared as distinct purple blue spots on membrane A (the anti-*Legionella* treatment). No spots were observed on the control membrane B which had been incubated with a control rabbit antibody. Spots were recorded using a digital camera and were counted for further analysis.

Various serogroups of *Legionella* can be identified by choosing appropriate sero group specific antibody. Mouse anti-*Legionella pneumophila* sero group 1 monoclonal antibody, (conjugated or unconjugated) can be obtained from BIODESIGN International (Saco, Maine). Custom-made antibodies can be obtained from a variety of manufacturers, including Strategic Diagnostics Inc., (Newark, Delaware). Serogroup specific or isolate specific antibodies or a mixture of antibodies can be used to detect a sample suspected of *Legionella* contamination. Polyclonal or monoclonal antibodies, either individually or in a mixture are capable of detecting various serogroups and isolates of *Legionella* that include *L. pneumophila* serogroups 1-13, *L. longbeachae*, *L. bozemanii*, *L. micdadei*, *L. dumoffii*, *L. feeleii*, *L. wadsworthii*, and *L. anisa*.

Example 5

Field Sampler For Viable *Legionella* Bacteria Shipped to a Laboratory
Required Materials
For each water sample location:
1. One sterile 100 ml vial w/sodium thiosulfate tablet;
2. Two sterile field sampler dip-slides;
3. Two authenticity labels sample with documentation;
4. HCl/KCl buffer made according to Standard Method specifications in dropper bottle; and
5. Safety equipment (safe glasses and gloves)
Field Sampler Labeling
1. For each field sampler, assign a tracking number and submit the sample submission spreadsheet with all water sample information.
2. Two field samplers are required per water sample location; one field sampler is used before and the other is used after acid treatment.
3. Affix completed label vertically (length-wise) onto the plastic dip-slide container.
Water Sample Collection and Field Sampler Processing
1. Collect 100 ml water sample in sterile vial, close securely, and invert to mix to completely dissolve sodium thiosulfate tablet (2-3 minutes);
2. After collecting water sample, immediately dip first dip-slide into the vial for 3 seconds, remove from water, and replace into original labeled canister;
3. Label this canister as non-acid treated by circling "N" on the label (detects total viable heterotrophic aerobic bacteria); and
4. Add required amount of pH adjust to water sample (1 ml to potable water, 2 ml to utility samples) while wearing safety goggles and gloves.
4. Securely close the vial, invert to mix, and wait exactly 5 minutes for acid incubation.
5. After 5 minutes, dip second field sampler into the acid treated sample for 3 seconds, remove from water, and replace into labeled canister (label canister as acid treated by circling "Y" on the label (detects viable *Legionella*).
6. Empty water sample from sterile vial and discard vial in trash.
7. Ship dip-slides to laboratory with appropriate packaging.
Interpretation of Results
Typically in well-managed potable water systems, the total viable heterotrophic aerobic bacterial concentration should be less than 1,000 CFU/ml and the viable *Legionella* bacteria concentration should be less than detectable (10 CFU/ml) by the methods disclosed. Typically in well-managed utility water systems (such as cooling water towers), the total viable heterotrophic aerobic bacterial concentration should be less than 10,000 CFU/ml and the viable *Legionella* concentration should be less than detectable (10 CFU/ml).

Publications Cited

The following are incorporated by reference to the extent they relate materials and methods disclosed herein.
Anonymous. 1998. "Water quality—detection and enumeration of *Legionella*", ISO International Organisation for Standardisation" 11731:1998, Geneva, Switzerland.
Anonymous. 1998. "Waters—examination for *Legionellae*," AS/NZS 3896:1998. Standards Australia, North Sydney, NSW, Australia.

I claim:
1. A dip-slide detection system for rapidly quantifying viable *Legionella* bacteria and total heterotrophic aerobic bacteria in a sample, the system comprising:
    a) a dip-slide comprising an absorbent medium, wherein the absorbent medium comprises nutrients for culturing *Legionella*, and separately also comprising at least one agent to selectively inhibit the growth of non-*Legionella* microorganisms, wherein the dip-slide is adapted to absorb a predetermined amount of the sample; and
    b) a detection reagent to quantify the amount of viable *Legionella* bacteria in the sample, wherein the detection reagent inhibits the growth of non-*Legionella* microorganisms.
2. A dip-slide for rapidly quantifying viable *Legionella* bacteria in a sample, the slide comprising an absorbent medium, nutrients for *Legionella* bacteria, and separately at least one agent to selectively inhibit the growth of non-*Legionella* microorganisms, and wherein the dip-slide is adapted to absorb a predetermined amount of the sample.
3. The dip-slide of claim 2, wherein the absorbent medium comprises agarose in a concentration of about 0.5 wt % to about 10.0 wt %.
4. The dip-slide of claim 2, wherein the dip-slide is adapted to absorb about 0.3 ml in about 60 seconds.

* * * * *